United States Patent
Pretz

(10) Patent No.: US 11,479,521 B2
(45) Date of Patent: *Oct. 25, 2022

(54) METHODS FOR MAKING LIGHT OLEFINS FROM DIFFERENT FEED STREAMS

(71) Applicant: Dow Global Technologies LLC, Midland, MI (US)

(72) Inventor: Matthew T. Pretz, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/491,318

(22) PCT Filed: Mar. 9, 2018

(86) PCT No.: PCT/US2018/021658
§ 371 (c)(1),
(2) Date: Sep. 5, 2019

(87) PCT Pub. No.: WO2018/169769
PCT Pub. Date: Sep. 20, 2018

(65) Prior Publication Data
US 2020/0017427 A1    Jan. 16, 2020

Related U.S. Application Data

(60) Provisional application No. 62/470,567, filed on Mar. 13, 2017.

(51) Int. Cl.
*C07C 5/333* (2006.01)
*C07C 4/06* (2006.01)
(Continued)

(52) U.S. Cl.
CPC .......... *C07C 5/3337* (2013.01); *B01J 8/0035* (2013.01); *B01J 8/1827* (2013.01); *B01J 8/26* (2013.01);
(Continued)

(58) Field of Classification Search
None
See application file for complete search history.

(56) References Cited

U.S. PATENT DOCUMENTS

| 4,051,013 A | 9/1977 | Strother |
| 4,579,716 A | 4/1986 | Krambeck et al. |

(Continued)

FOREIGN PATENT DOCUMENTS

| CA | 2617580 C | 2/2014 |
| CA | 2990639 A1 | 12/2016 |

(Continued)

OTHER PUBLICATIONS

Andersen, Jim "Technologies for Filling the Propylene Gap" 2005 UOP pp. 1-19 (Year: 2005).*

(Continued)

*Primary Examiner* — Philip Y Louie
(74) *Attorney, Agent, or Firm* — Dinsmore & Shohl LLP

(57) ABSTRACT

According to one or more embodiments of the present disclosure, chemical streams may be processed by a method which may comprise operating a first chemical process, stopping the first chemical process and removing the first catalyst from the reactor, and operating a second chemical process. The reaction of the first chemical process may be a dehydrogenation reaction, a cracking reaction, a dehydration reaction, or a methanol-to-olefin reaction. The reaction of the second chemical process may be a dehydrogenation reaction, a cracking reaction, a dehydration reaction, or a methanol-to-olefin reaction. The first reaction and the second reaction may be different types of reactions.

17 Claims, 3 Drawing Sheets

(51) Int. Cl.
  *C07C 1/24* (2006.01)
  *B01J 8/18* (2006.01)
  *B01J 8/00* (2006.01)
  *B01J 8/26* (2006.01)
  *C07C 1/22* (2006.01)

(52) U.S. Cl.
  CPC ............... *C07C 1/22* (2013.01); *C07C 1/24* (2013.01); *C07C 4/06* (2013.01); *B01J 2208/00761* (2013.01); *C07C 2523/08* (2013.01); *C07C 2523/42* (2013.01); *C07C 2523/62* (2013.01); *C07C 2529/40* (2013.01); *C07C 2529/85* (2013.01)

(56) References Cited

U.S. PATENT DOCUMENTS

| | | | |
|---|---|---|---|
| 4,595,567 | A | 6/1986 | Hedrick |
| 5,190,650 | A | 3/1993 | Tammera et al. |
| 5,275,641 | A | 1/1994 | Tammera et al. |
| 5,456,821 | A | 10/1995 | Absil et al. |
| 7,128,827 | B2 | 10/2006 | Tailman et al. |
| 7,396,971 | B2 | 8/2008 | Smith et al. |
| 7,491,315 | B2 | 2/2009 | Eng et al. |
| 7,575,725 | B2 | 8/2009 | Lomas et al. |
| 7,585,489 | B2 | 9/2009 | Abrevaya et al. |
| 8,157,985 | B2 | 4/2012 | Nicholas et al. |
| 8,669,406 | B2 | 3/2014 | Pretz et al. |
| 9,284,235 | B2 | 3/2016 | Liu et al. |
| 9,370,759 | B2 | 6/2016 | Pretz et al. |
| 9,725,382 | B2 | 8/2017 | Pretz et al. |
| 2002/0024276 | A1 | 2/2002 | Smith et al. |
| 2004/0024276 | A1* | 2/2004 | Smith ............ C10G 3/62 585/640 |
| 2004/0104148 | A1 | 6/2004 | Lomas et al. |
| 2010/0016648 | A1 | 1/2010 | Qi et al. |
| 2011/0112345 | A1 | 5/2011 | Chewier et al. |
| 2011/0251046 | A1 | 10/2011 | Niccum et al. |
| 2011/0275874 | A1 | 11/2011 | Li et al. |
| 2014/0115952 | A1 | 5/2014 | Wang et al. |
| 2014/0275675 | A1 | 9/2014 | Eng |
| 2016/0272559 | A1 | 9/2016 | Pretz et al. |
| 2016/0362613 | A1 | 12/2016 | Cunningham et al. |

FOREIGN PATENT DOCUMENTS

| | | | | |
|---|---|---|---|---|
| CN | 203448073 | U | 2/2014 | |
| CN | 104437274 | A | 3/2015 | |
| EP | 127116 | B1 | 7/1988 | |
| EP | 2172440 | A1 | 4/2010 | |
| EP | 1555308 | B1 | 10/2010 | |
| IN | 253588 | | 8/2012 | |
| IN | 201404173 | P1 | 4/2016 | |
| WO | WO-2015073152 | A1 * | 5/2015 | ........... C07C 5/3337 |
| WO | 2017058854 | A1 | 4/2017 | |

OTHER PUBLICATIONS

International Search Report and Written Opinion pertaining to PCT/US2018/021658, dated Jun. 6, 2018.
International Search Report and Written Opinion pertaining to PCT/US2018/021656, dated May 14, 2018.
Zamostny et al., "A Multipurpose Micro-pulse Reactor for Studying Gas-phase Reactions", Chemical and Biochemical Engineering Quarterly, 2007, 107-108.
Examination Report pertaining to corresponding G.C.C. Patent Application No. GC 2018-34837, dated Aug. 26, 2019.
Office Action dated Apr. 9, 2020 pertaining to U.S. Appl. No. 16/491,331, filed Sep. 5, 2019, 32 pgs.
Examination Report pertaining to GCC 2018-34838, dated Nov. 27, 2019.
Office Action dated Oct. 19, 2020 pertaining to U.S. Appl. No. 16/491,331, filed Sep. 5, 2019, 30 pgs.
Examination Report pertaining to G.C.C. Patent Application No. 2018-34838, dated Oct. 6, 2020.
Office Action dated Apr. 26, 2021 pertaining to U.S. Appl. No. 16/491,331, filed Sep. 5, 2019, 23 pgs.
U.S. Office Action dated Nov. 29, 2021 pertaining to U.S. Appl. No. 16/491,331, filed Sep. 5, 2019, 21 pages.
Chinese Office Action dated Nov. 11, 2021 pertaining to Chinese Application No. 201880012341.7 filed Mar. 9, 2018, 7 pages.
Chinese Search Report dated Nov. 11, 2021 pertaining to Chinese Application No. 201880012341.7 filed filed Mar. 9, 2018, 2 pages.
Article 94(3) dated May 4, 2022, pertaining to EP Patent Application No. 18712415.1, 6 pgs.

* cited by examiner

METHODS FOR MAKING LIGHT OLEFINS FROM DIFFERENT FEED STREAMS

This application claims priority to U.S. Provisional Patent Application No. 62/470,567, filed Mar. 13, 2017, entitled "Methods For Making Light Olefins From Different Feed Streams", the contents of which are hereby incorporated by reference in their entirety.

BACKGROUND

Field

The present disclosure generally relates to chemical processing, and more specifically, to reactor designs and systems utilized in reactions to from light olefins.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. However, most light olefins must be produced by different reaction processes based on the given chemical feed stream, which may be a product stream from a crude oil refining operation.

BRIEF SUMMARY

There is a continued need for processes and apparatuses which are suitable for producing light olefins from varying feed streams. Light olefins may be produced from a variety of feed stream by utilizing different catalysts. For example, light olefins may be produced by at least dehydrogenation reactions, cracking reactions, dehydration reactions, and methanol-to-olefin reactions. However, according to various embodiments, these reaction types may utilize different feed streams which are subsequently reacted to form the light olefins. Non-limiting examples include utilizing a dehydrogenation reaction that may utilize a gallium and/or platinum catalyst to react a feed stream comprising one or more of ethane, propane, n-butane, and i-butane; a cracking reaction that may utilize a zeolite catalyst to react a feed stream comprising one or more of naphtha, n-butane, or i-butane; a dehydration reaction that may utilize an acid catalyst (such as alumina or zeolite) to react a feed stream comprising one or more of ethanol, propanol, or butanol; and a methanol-to-olefin reaction that may utilize a zeolite catalyst (such as SAPO-34) to react a feed stream comprising methanol.

While numerous reaction types, as described above, may be utilized to produce light olefins (e.g., dehydrogenation, cracking, dehydration, and methanol-to-olefin), a need exists for a flexible reactor system which can efficiently handle two or more of these types of reactions. For example, a flexible reactor system which can handle two or more of dehydrogenation, cracking, dehydration, and methanol-to-olefin reactions allows for the system to utilize varying feeds as they become available or change price without the added capital costs of having different reactor systems to treat each feedstock.

Described herein, according to one or more embodiments, are methods for processing different chemical feed streams in a single reactor to form light olefins. The reactor designs described herein may be operable for processing at least two different feed steams at different times, utilizing different types of reactions for each feed stream, to form light olefins. Such methods and systems may reduce costs for producing light olefins by allowing for the selection of a feed stream and reaction type which is most economical while not requiring the added capital costs of designing and constructing a completely separate chemical reactor system.

According to one embodiment, chemical streams may be processed by a method which may comprise operating a first chemical process, stopping the first chemical process and removing the first catalyst from the reactor, and operating a second chemical process. Operating a first chemical process may comprise contacting a first feed stream with a first catalyst in a reactor. The contacting of the first feed stream with the first catalyst may cause a first reaction which forms a first product stream. Operating a second chemical process may comprise contacting a second feed stream with a second catalyst in the reactor. The contacting of the second feed stream with the second catalyst may cause a second reaction which forms a second product stream. The reactor may comprise an upstream reactor section and a downstream reactor section. The upstream reactor section may have an average cross-sectional area that is at least 150% of the average cross-sectional area of the downstream reactor section. The first reaction may be a dehydrogenation reaction, a cracking reaction, a dehydration reaction, or a methanol-to-olefin reaction. The second reaction may be a dehydrogenation reaction, a cracking reaction, a dehydration reaction, or a methanol-to-olefin reaction. The first reaction and the second reaction may be different types of reactions.

According to another embodiment, chemical streams may be processed by a method which may comprise operating a first chemical process, stopping the first chemical process and removing the first catalyst from the reactor, and operating a second chemical process. Operating a first chemical process may comprise contacting a first feed stream with a first catalyst in a reactor. The contacting of the first feed stream with the first catalyst may cause a first reaction which forms a first product stream. Operating a second chemical process may comprise contacting a second feed stream with a second catalyst in the reactor. The contacting of the second feed stream with the second catalyst may cause a second reaction which forms a second product stream. The reactor may comprise an upstream reactor section and a downstream reactor section. The upstream reactor section may have an average cross-sectional area that is at least 150% of the average cross-sectional area of the downstream reactor section. The first reaction may be a cracking reaction and the second reaction may be a dehydrogenation reaction.

According to yet another embodiment, chemical streams may be processed by a method which may comprise operating a first chemical process, stopping the first chemical process and removing the first catalyst from the reactor, and operating a second chemical process. Operating a first chemical process may comprise contacting a first feed stream with a first catalyst in a reactor. The contacting of the first feed stream with the first catalyst may cause a first reaction which forms a first product stream. Operating a second chemical process may comprise contacting a second feed stream with a second catalyst in the reactor. The contacting of the second feed stream with the second catalyst may cause a second reaction which forms a second product stream. The reactor may comprise an upstream reactor section and a downstream reactor section. The upstream reactor section may have an average cross-sectional area that is at least 150% of the average cross-sectional area of the downstream reactor section. The first reaction may be a dehydrogenation reaction and the second reaction may be a cracking reaction.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
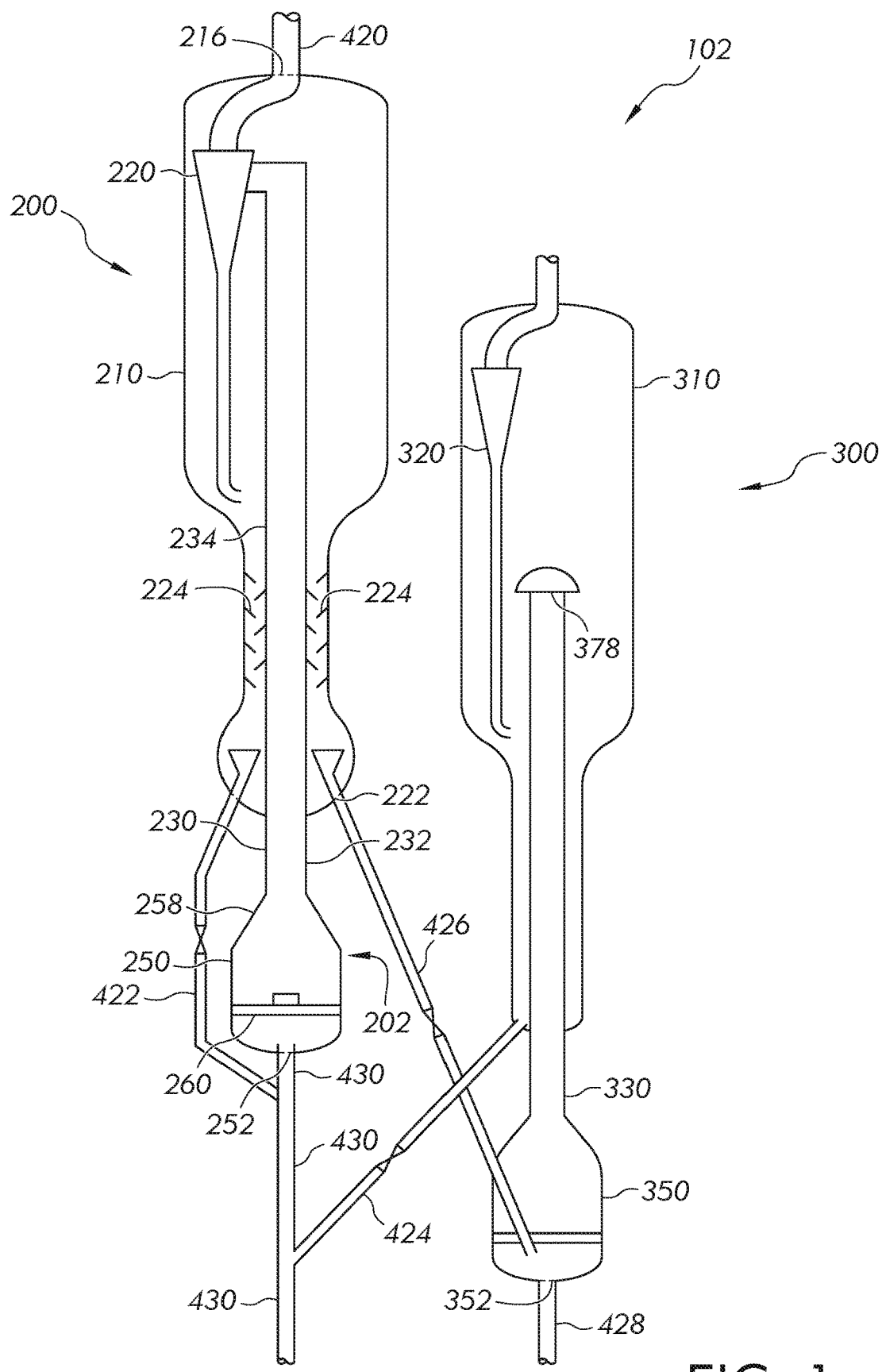
FIG. 1 schematically depicts a reactor system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments related to methods for processing chemical streams to form light olefins are disclosed herein. In various embodiments, two different chemical feed streams may be processed sequentially in a single flexible reactor system, where each feed stream has a different composition. Since each feed stream has a different composition, different reaction types may be required to form light olefins from the respective feed streams, and different catalysts may be utilized in each type of reaction. As described herein, a "type" of reaction refers to a class of reaction that imparts a particular change on some or all of the components of a feed stream. For example, one type of reaction described herein is a dehydrogenation reaction. Other example reaction types include cracking, dehydration, and methanol-to-olefin reactions. Additionally, as described herein, the "first feed stream" refers to an initial feed stream which is processed in a reactor, and the "second feed stream" refers to a sequential feed stream (i.e., a stream which is processed chronologically after the first feed stream) which is processed in the same reactor. For example, a first feed stream may be processed in the reactor, and then, later, a second feed stream may be processed in the reactor following the removal of the first feed stream.

The first feed stream may be converted to light olefins by contact with a first catalyst, and the second feed stream may be converted to light olefins by a second catalyst. Additionally, in embodiments, the first feed stream may be processed by the first catalyst to form a first product stream, in what is referred to as the first reaction, and the second feed stream may be processed by the second catalyst to form a second product stream, in what is referred to as the second reaction. The first reaction of the first feed stream to form the first product stream may be referred to as the "first chemical process," and the second reaction of the second feed stream to form the second product stream may be referred to as the "second chemical process."

According to one or more embodiments, a method for processing chemical streams may include a step of operating the first chemical process involving the first reaction, stopping the first chemical process and removing the first catalyst from the reactor, and operating the second chemical process involving the second reaction. These steps may occur in chronological order as listed. According to one or more embodiments, the first reaction may be a dehydrogenation reaction, a cracking reaction, a dehydration reaction, or a methanol-to-olefin reaction, and the second reaction may be a dehydrogenation reaction, a cracking reaction, a dehydration reaction, or a methanol-to-olefin reaction. However, in embodiments, the first reaction and the second reaction are different types of reactions. Additionally, in one or more embodiments, the first catalyst and the second catalyst may have different compositions.

For example, if the first reaction is a dehydrogenation reaction, then the second reaction may be a cracking reaction, a dehydration reaction, or a methanol-to-olefin reaction, but not a dehydrogenation catalyst. In another embodiment, if the first reaction is a cracking reaction, then the second reaction may be a dehydrogenation reaction, a dehydration reaction, or a methanol-to-olefin reaction, but not a cracking catalyst. In another embodiment, if the first reaction is a dehydration reaction, then the second reaction may be a dehydrogenation reaction, a cracking reaction, or a methanol-to-olefin reaction, but not a dehydration catalyst. In another embodiment, if the first reaction is a methanol-to-olefin reaction, then the second reaction may be a dehydrogenation reaction, a cracking reaction, or a dehydration reaction, but not a methanol-to-olefin catalyst.

According to one or more embodiments, the first reaction or the second reaction may be a dehydrogenation reaction. According to such embodiments, the first feed stream or the second feed stream may comprise one or more of ethane, propane, n-butane, and i-butane. For example, if the first reaction is a dehydrogenation reaction, then the first feed stream may comprise one or more of ethane, propane, n-butane, and i-butane, and if the second reaction is a dehydrogenation reaction, then the second feed stream may comprise one or more of ethane, propane, n-butane, and i-butane. According to one or more embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of ethane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of propane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of the sum of ethane, propane, n-butane, and i-butane.

In one or more embodiments, the dehydrogenation reaction may utilize gallium and/or platinum catalyst as a catalyst. In such embodiments, the first catalyst or the second catalyst may comprise a gallium and/or platinum catalyst. For example, if the first reaction is a dehydrogenation reaction, then the first catalyst may comprise gallium and/or platinum catalyst, and if the second reaction is a dehydrogenation reaction, then the second catalyst may comprise gallium and/or platinum catalyst. As described herein, a gallium and/or platinum catalyst comprises gallium, platinum, or both. The gallium and/or platinum catalyst may be carried by an alumina or alumina silica support, and may optionally comprise potassium. Such gallium and/or platinum catalysts are disclosed in U.S. Pat. No. 8,669,406, which is incorporated herein by reference in its entirety. However, it should be understood that other suitable catalysts may be utilized to perform the dehydrogenation reaction.

According to one or more embodiments, the first reaction or the second reaction may be a cracking reaction. According to such embodiments, the first feed stream or the second feed stream may comprise one or more of naphtha, n-butane, or i-butane. For example, if the first reaction is a cracking reaction, then the first feed stream may comprise one or more of naphtha, n-butane, or i-butane, and if the second reaction is a cracking reaction, then the second feed stream may comprise one or more of naphtha, n-butane, or i-butane. According to one or more embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of naphtha. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of the sum of naphtha, n-butane, and i-butane.

In one or more embodiments, the cracking reaction may utilize one or more zeolites as a catalyst. In such embodiments, the first catalyst or the second catalyst may comprise one or more zeolites. For example, if the first reaction is a cracking reaction, then the first catalyst may comprise one or more zeolites, and if the second reaction is a cracking reaction, then the second catalyst may comprise one or more zeolites. In some embodiments, the one or more zeolites utilized in the cracking reaction may comprise a ZSM-5 zeolite. However, it should be understood that other suitable catalysts may be utilized to perform the cracking reaction. For example, suitable catalysts that are commercially available may include Intercat Super Z Excel or Intercat Super Z Exceed. In additional embodiments, the cracking catalyst may comprise, in addition to a catalytically active material, platinum. For example, the cracking catalyst may include from 0.001 wt. % to 0.05 wt. % of platinum. The platinum may be sprayed on as platinum nitrate and calcined at an elevated temperature, such as around 700° C. Without being bound by theory, it is believed that the addition of platinum to the catalyst may allow for easier combustion of supplemental fuels, such as methane.

According to one or more embodiments, the first reaction or the second reaction may be a dehydration reaction. According to such embodiments, the first feed stream or the second feed stream may comprise one or more of ethanol, propanol, or butanol. For example, if the first reaction is a dehydration reaction, then the first feed stream may comprise one or more of ethanol, propanol, or butanol, and if the second reaction is a dehydration reaction, then the second feed stream may comprise one or more of ethanol, propanol, or butanol. According to one or more embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of ethanol. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of propanol. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of butanol. In additional embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of the sum of ethanol, propanol, and butanol.

In one or more embodiments, the dehydration reaction may utilize one or more acid catalysts. In such embodiments, the first catalyst or the second catalyst may comprise one or more acid catalysts. For example, if the first reaction is a dehydration reaction, then the first catalyst may comprise one or more acid catalysts, and if the second reaction is a dehydration reaction, then the second catalyst may comprise one or more acid catalysts. In some embodiments, the one or more acid catalysts utilized in the dehydration reaction may comprise a zeolite (such as ZSM-5 zeolite), alumina, amorphous aluminosilicate, acid clay, or combinations thereof. For example, commercially available alumina catalysts which may be suitable, according to one or more embodiments, include SynDol (available from Scientific Design Company), V200 (available from UOP), or P200 (available from Sasol). Commercially available zeolite catalysts which may be suitable include CBV 8014, CBV 28014 (each available from Zeolyst). Commercially available amorphous aluminosilicate catalysts which may be suitable include silica-alumina catalyst support, grade 135 (available from Sigma Aldrich). However, it should be understood that other suitable catalysts may be utilized to perform the dehydration reaction.

According to one or more embodiments, the first reaction or the second reaction may be a methanol-to-olefin reaction. According to such embodiments, the first feed stream or the second feed stream may comprise methanol. For example, if the first reaction is a methanol-to-olefin reaction, then the first feed stream may comprise methanol, and if the second reaction is a methanol-to-olefin reaction, then the second feed stream may comprise methanol. According to one or more embodiments, the first feed stream or the second feed stream may comprise at least 50 wt. %, at least 60 wt. %, at least 70 wt. %, at least 80 wt. %, at least 90 wt. %, at least 95 wt. % or even at least 99 wt. % of methanol.

In one or more embodiments, the methanol-to-olefin reaction may utilize one or more zeolites as a catalyst. In such embodiments, the first catalyst or the second catalyst may comprise one or more zeolites. For example, if the first reaction is a methanol-to-olefin reaction, then the first catalyst may comprise one or more zeolites, and if the second reaction is a methanol-to-olefin reaction, then the second catalyst may comprise one or more zeolites. In some embodiments, the one or more zeolites utilized in the methanol-to-olefin reaction may comprise a one or more of a ZSM-5 zeolite or a SAPO-34 zeolite. However, it should be understood that other suitable catalysts may be utilized to perform the methanol-to-olefin reaction.

According to various embodiments, the first product stream and the second product stream may each comprise light olefins. As described herein, "light olefins" refers to one or more of ethylene, propylene, or butene. As described herein, butene many include any isomer of butene, such as α-butylene, cis-β-butylene, trans-β-butylene, and isobutylene.

In one or more embodiments, the operating of the first chemical process may include passing the first product stream out of the reactor. Additionally, in one or more embodiments, the operating of the second chemical process may include passing the second product stream out of the reactor. In one embodiment, the first product stream may comprise at least 50 wt. % light olefins. For example, the first product stream may comprise at least 60 wt. % light olefins, at least 70 wt. % light olefins, at least 80 wt. % light olefins, at least 90 wt. % light olefins, at least 95 wt. % light olefins, or even at least 99 wt. % light olefins. In another embodiment, the second product stream may comprise at least 50 wt. % light olefins. For example, the second product stream may comprise at least 60 wt. % light olefins, at least 70 wt. % light olefins, at least 80 wt. % light olefins, at least 90 wt. % light olefins, at least 95 wt. % light olefins, or even at least 99 wt. % light olefins.

Now referring to FIG. 1, an example reactor system 102 which may be suitable for use with the methods described herein is schematically depicted. It should be understood that, in some embodiments, the first chemical process and the second chemical process may be operated sequentially in the reactor system 102. However, with reference to the description of FIG. 1, it should be understood that any description of a catalyst, feed stream, or product stream, may equally apply to the first chemical process or the second chemical process. For example, a "catalyst" in FIG. 1 may refer to the first catalyst or the second catalyst, the "feed stream" may refer to the first feed stream or second feed stream, and the "product stream" may refer to the first product stream or the second product stream.

Now referring to FIG. 1, an example reactor system 102 which may be suitable for use with the methods described herein is schematically depicted, and it should be understood that other reactor system configurations may be suitable for the methods described herein. The reactor system 102 generally comprises multiple system components, such as a reactor portion 200 and/or a catalyst processing portion 300. As used herein in the context of FIG. 1, the reactor portion 200 generally refers to the portion of a reactor system 102 in which the major process reaction takes place, such as a dehydrogenation reaction, a cracking reaction, a dehydration reaction, or a methanol-to-olefin reaction to form light olefins. The reactor portion 200 comprises a reactor 202 which may include a downstream reactor section 230 and an upstream reactor section 250. According to one or more embodiments, as depicted in FIG. 1, the reactor portion 200 may additionally include a catalyst separation section 210 which serves to separate the catalyst from the chemical products formed in the reactor 202. Also, as used herein, the catalyst processing portion 300 generally refers to the portion of a reactor system 102 where the catalyst is in some way processed, such as by combustion. The catalyst processing portion 300 may comprise a combustor 350 and a riser 330, and may optionally comprise a catalyst separation section 310. In some embodiments, the catalyst may be regenerated by burning off contaminants like coke in the catalyst processing portion 300. In additional embodiments, the catalyst may be heated in the catalyst processing portion 300. A supplemental fuel may be utilized to heat the catalyst in the catalyst processing portion 300 if coke or another combustible material is not formed on the catalyst, or an amount of coke formed on the catalyst is not sufficient to burn off to heat the catalyst to a desired temperature. In one or more embodiments, the catalyst separation section 210 may be in fluid communication with the combustor 350 (e.g., via standpipe 426) and the catalyst separation section 310 may be in fluid communication with the upstream reactor section 250 (e.g., via standpipe 424 and transport riser 430).

As described with respect to FIG. 1, the feed stream may enter transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed contacts the catalyst in the upstream reactor section 250, and each flow upwardly into and through the downstream reactor section 230 to produce a chemical product. The chemical product and the catalyst may be passed out of the downstream reactor section 230 to a separation device 220 in the catalyst separation section 210, where the catalyst is separated from the chemical product, which is transported out of the catalyst separation section 210. The separated catalyst is passed from the catalyst separation section 210 to the combustor 350. In the combustor 350, the catalyst may be processed by, for example, combustion. For example, and without limitation, the catalyst may be de-coked and/or supplemental fuel may be combusted to heat the catalyst. The catalyst is then passed out of the combustor 350 and through the riser 330 to a riser termination separator 378, where the gas and solid components from the riser 330 are at least partially separated. The vapor and remaining solids are transported to a secondary separation device 320 in the catalyst separation section 310 where the remaining catalyst is separated from the gases from the catalyst processing (e.g., gases emitted by combustion of spent catalyst or supplemental fuel). The separated catalyst is then passed from the catalyst separation section 310 to the upstream reactor section 250 via standpipe 424 and transport riser 430, where it is further utilized in a catalytic reaction. Thus, the catalyst, in operation, may cycle between the reactor portion 200 and the catalyst processing portion 300. In general, the processed chemical streams, including the feed streams and product streams may be gaseous, and the catalyst may be fluidized particulate solid.

According to one or more embodiments described herein, the reactor portion 200 may comprise an upstream reactor section 250, a transition section 258, and a downstream reactor section 230, such as a riser. The transition section 258 may connect the upstream reactor section 250 with the downstream reactor section 230. According to one or more embodiments, the upstream reactor section 250 and the downstream reactor section 230 may each have a substantially constant cross-section area, while the transition section 258 may be tapered and does not have a constant cross-sectional area. As described herein, unless otherwise explicitly stated, the "cross-sectional area" refers to the area of the cross section of a portion of the reactor part in a plane substantially orthogonal to the direction of general flow of reactants and/or products. For example, in FIG. 1, the cross sectional area of the upstream reactor section 250, the transition section 258, and the downstream reactor section 230 is in the direction of a plane defined by the horizontal direction and the direction into the page (orthogonal to the direction of fluid motion, i.e., vertically upward in FIG. 1).

As depicted in FIG. 1, the upstream reactor section 250 may be positioned below the downstream reactor section 230. Such a configuration may be referred to as an upflow configuration in the reactor 202.

As described herein, the upstream reactor section 250 may include a vessel, drum, barrel, vat, or other container suitable for a given chemical reaction. In one or more embodiments, the upstream reactor section 250 may be generally cylindrical in shape (i.e., having a substantially circular cross-sectional shape), or may alternately be non-cylindrically shaped, such as prism shaped with cross-sectional shapes of triangles, rectangles, pentagons, hexagons, octagons, ovals, or other polygons or curved closed shapes, or combinations thereof. The upstream reactor section 250, as used throughout this disclosure, may generally include a metallic frame, and may additionally include refractory linings or other materials utilized to protect the metallic frame and/or control process conditions. As depicted in FIG. 1, the upstream reactor section 250 may include a lower reactor portion catalyst inlet port 252 defining the connection of transport riser 430 to the upstream reactor section 250.

The upstream reactor section 250 may be connected to a transport riser 430 which, in operation, may provide processed catalyst and/or reactant chemicals in a feed stream to the reactor portion 200. The processed catalyst and/or reactant chemicals may be mixed with a feed distributor 260 housed in the upstream reactor section 250. The catalyst entering the upstream reactor section 250 via transport riser 430 may be passed through standpipe 424 to a transport riser 430, thus arriving from the catalyst processing portion 300. In some embodiments, catalyst may come directly from the catalyst separation section 210 via standpipe 422 and into a transport riser 430, where it enters the upstream reactor section 250. This catalyst may be slightly deactivated, but may still, in some embodiments, be suitable for reaction in the upstream reactor section 250. As used herein, "deactivated" may refer to a catalyst which is contaminated with a substance such as coke, or is cooler in temperature than desired. Regeneration may remove the contaminant such as coke, raise the temperature of the catalyst, or both.

In one or more embodiments, the feed distributor 260 may be operable to dispense the first feed stream and the second feed stream at all shroud distributor velocities from 200 ft/s to 80 ft/s. In such embodiments, various feed streams may be utilized while maintaining the desired reactor characteristics, such as operating as a fast fluidized, turbulent, or bubbling bed reactor in the upstream reactor section 250 and as a dilute phase riser reactor in the downstream reactor section 230. For example, according to one or more embodiments, a shroud distributor velocity of about 80 ft/s may be utilized in the upstream reactor section 250 for naphtha feeds, while a shroud distributor velocity of about 200 ft/s may be utilized in the upstream reactor section 230 for propane feeds. In additional embodiments, some orifices could be closed in the reactor 202 when naphtha is utilized as a feed stream. The "shroud distributor velocity" refers the velocity at which the gas exits the distributor, sometimes through a shroud. For example, suitable distributors are disclosed in U.S. Pat. No. 9,370,759, the teachings of which are incorporated herein by reference in their entirety.

Still referring to FIG. 1, the reactor portion 200 may comprise a downstream reactor section 230 which acts to transport reactants, products, and/or catalyst from the upstream reactor section 250 to the catalyst separation section 210. In one or more embodiments, the downstream reactor section 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The downstream reactor section 230, as used throughout this disclosure, may generally include a metallic frame, and may additionally include refractory linings or other materials utilized to protect the metallic frame and/or control process conditions.

According to some embodiments, the downstream reactor section 230 may include an external riser section 232 and an internal riser section 234. As used herein, an "external riser section" refers to the portion of the riser that is outside of the catalyst separation section, and an "internal riser section" refers to the portion of the riser that is within the catalyst separation section. For example, in the embodiment depicted in FIG. 1, the internal riser section 234 of the reactor portion 200 may be positioned within the catalyst separation section 210, while the external riser section 232 is positioned outside of the catalyst separation section 210.

As depicted in FIG. 1, the upstream reactor section 250 may be connected to the downstream reactor section 230 via the transition section 258. The upstream reactor section 250 may generally comprise a greater cross-sectional area than the downstream reactor section 230. The transition section 258 may be tapered from the size of the cross-section of the upstream reactor section 250 to the size of the cross-section of the downstream reactor section 230 such that the transition section 258 projects inwardly from the upstream reactor section 250 to the downstream reactor section 230.

In some embodiments, such as those where the upstream reactor section 250 and the downstream reactor section 230 have similar cross-sectional shapes, the transition section 258 may be shaped as a frustum. For example, for an embodiment of a reactor portion 200 comprising a cylindrical upstream reactor section 250 and cylindrical downstream reactor section 230, the transition section 258 may be shaped as a conical frustum. However, it should be understood that a wide variety of upstream reactor section 250 shapes are contemplated herein which connect various shapes and sizes of upstream reactor sections 250 and downstream reactor sections 230.

In one or more embodiments, the upstream reactor section 250 may have an average cross-sectional area that is at least 150% of the average cross-sectional area of the downstream reactor section 230. As described herein, an "average cross-sectional area" refers to the mean of the cross-sectional areas for a given system component or section such as the upstream reactor section 250 or the downstream reactor section 230. If the system component or section has a substantially constant cross-sectional area, such as the cylindrical shapes of the depicted upstream reactor section 250 or the downstream reactor section 230, then the cross-sectional area at any point is about equal to the average cross-sectional area.

According to one or more embodiments, the upstream reactor section 250 may have an average cross-sectional area that is at least 160%, at least 170%, at least 180%, at least 190%, at least 200%, at least 250%, at least 300%, at least 400% or even at least 500% of the average cross-sectional area of the downstream reactor section 230.

In one or more embodiments, based on the shape, size, and other processing conditions such as temperature and pressure in the upstream reactor section 250 and the downstream reactor section 230, the upstream reactor section 250 may operate in a manner that is or approaches isothermal, such as in a fast fluidized, turbulent, or bubbling bed reactor, while the downstream reactor section 230 may operate in more of a plug flow manner, such as in a dilute phase riser reactor. For example, the reactor 202 of FIG. 1 may comprise a upstream reactor section 250 operating as a fast fluidized, turbulent, or bubbling bed reactor and a downstream reactor section 230 operating as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime where the superficial velocity of less than the choking velocity and is more dense than the fast fluidized regime. As described herein, a "bubbling bed" reactor may refer to a fluidization regime wherein well defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, where the gas and catalyst have about the same velocity in a dilute phase.

In one or more embodiments, the pressure in the reactor 202 may range from 6.0 to 44.7 pounds per square inch absolute (psia, from about 41.4 kilopascals, kPa, to about 308.2 kPa), but in some embodiments, a narrower selected range, such as from 15.0 psia to 35.0 psia, (from about 103.4 kPa to about 241.3 kPa), may be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where a reactor comprises an upstream reactor section 250 that operates as a fast fluidized, turbulent, or bubbling bed reactor and a downstream reactor section 230 that operates as a riser reactor, the superficial gas velocity may range therein from 2 feet per second (ft/s, about 0.61 meters per second, m/s) to 80 ft/s (about 24.38 m/s), such as from 2 ft/s (about 0.61 m/s) to 10 ft/s (about 3.05 m/s), in the upstream reactor section 250, and from 30 ft/s (about 9.14 m/s) to 70 ft/s (about 21.31 m/s) in the downstream reactor section 230. In additional embodiments, a reactor configuration that is fully of a riser type may operate at a single high superficial gas velocity, for example, in some embodiments at least 30 ft/s (about 9.15 m/s) throughout.

In additional embodiments, the ratio of catalyst to feed stream in the reactor 202 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second ($lb/ft^2$-s) (about 4.89 $kg/m^2$-s) to 20 $lb/ft^2$-s (to about 97.7 kg/m2-s) in the upstream reactor section 250, and from 10 $lb/ft^2$-s (about 48.9 kg/m2-s) to 100 $lb/ft^2$-s (about 489 kg/m2-s) in the downstream reactor section 230.

In operation, the catalyst may move upward through the downstream reactor section 230 (from the upstream reactor section 250), and into the separation device 220. The separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation. In embodiments where the separation device 220 comprises more than one cyclonic separation stages, the first separation device into which the fluidized stream enters is referred to a primary cyclonic separation device. The fluidized effluent from the primary cyclonic separation device may enter into a secondary cyclonic separation device for further separation. Primary cyclonic separation devices may include, for example, primary cyclones, and systems commercially available under the names VSS (commercially available from UOP), LD2 (commercially available from Stone and Webster), and RS2 (commercially available from Stone and Webster). Primary cyclones are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional cyclones, e.g. secondary cyclones and tertiary cyclones, are employed for further separation of the catalyst from the product gas. It should be understood that any primary cyclonic separation device may be used in embodiments of the invention.

According to one or more embodiments, following separation from vapors in the separation device 220, the catalyst may generally move through the stripper 224 to the catalyst outlet port 222 where the catalyst is transferred out of the reactor portion 200 via standpipe 426 and into the catalyst processing portion 300. Optionally, the catalyst may also be transferred directly back into the upstream reactor section 250 via standpipe 422. Alternatively, the catalyst may be premixed with processed catalyst in the transport riser 430.

According to one or more embodiments, operating the first chemical process and/or second chemical process, such as in reactor system 102, may comprise recycling the catalyst utilized in the first or second chemical process by passing the catalyst from the reactor 202 to a regeneration unit (such as the combustor 350 of the embodiment of FIG. 1), processing the respective catalyst in the regeneration unit, and passing the first catalyst from the regeneration unit to the reactor 202.

Referring now to the catalyst processing portion 300, as depicted in FIG. 1, the combustor 350 of the catalyst processing portion 300 may include one or more lower reactor section inlet ports 352 and may be in fluid communication with the riser 330. The combustor 350 may be in fluid communication with the catalyst separation section 210 via standpipe 426, which may supply spent catalyst from the reactor portion 200 to the catalyst processing portion 300 for regeneration. The combustor 350 may include an additional lower reactor section inlet port 352 where air inlet 428 connects to the combustor 350. The air inlet 428 may supply reactive gases which may react with the spent catalyst or a supplemental fuel to at least partially regenerate the catalyst. For example, the catalyst may be coked following the reactions in the upstream reactor section 250, and the coke may be removed from the catalyst (i.e., regenerating the catalyst) by a combustion reaction. For example, oxidizer (such as air) may be fed into the combustor 350 via the air inlet 428. Alternatively or additionally, such as when coke is not formed on the catalyst, a supplemental fuel may be injected into the combustor 350, which may be burned to heat the catalyst. Following combustion, the processed catalyst may be separated in the catalyst separation section 310 and delivered back into the reactor portion 200 via standpipe 424.

Figure 2:
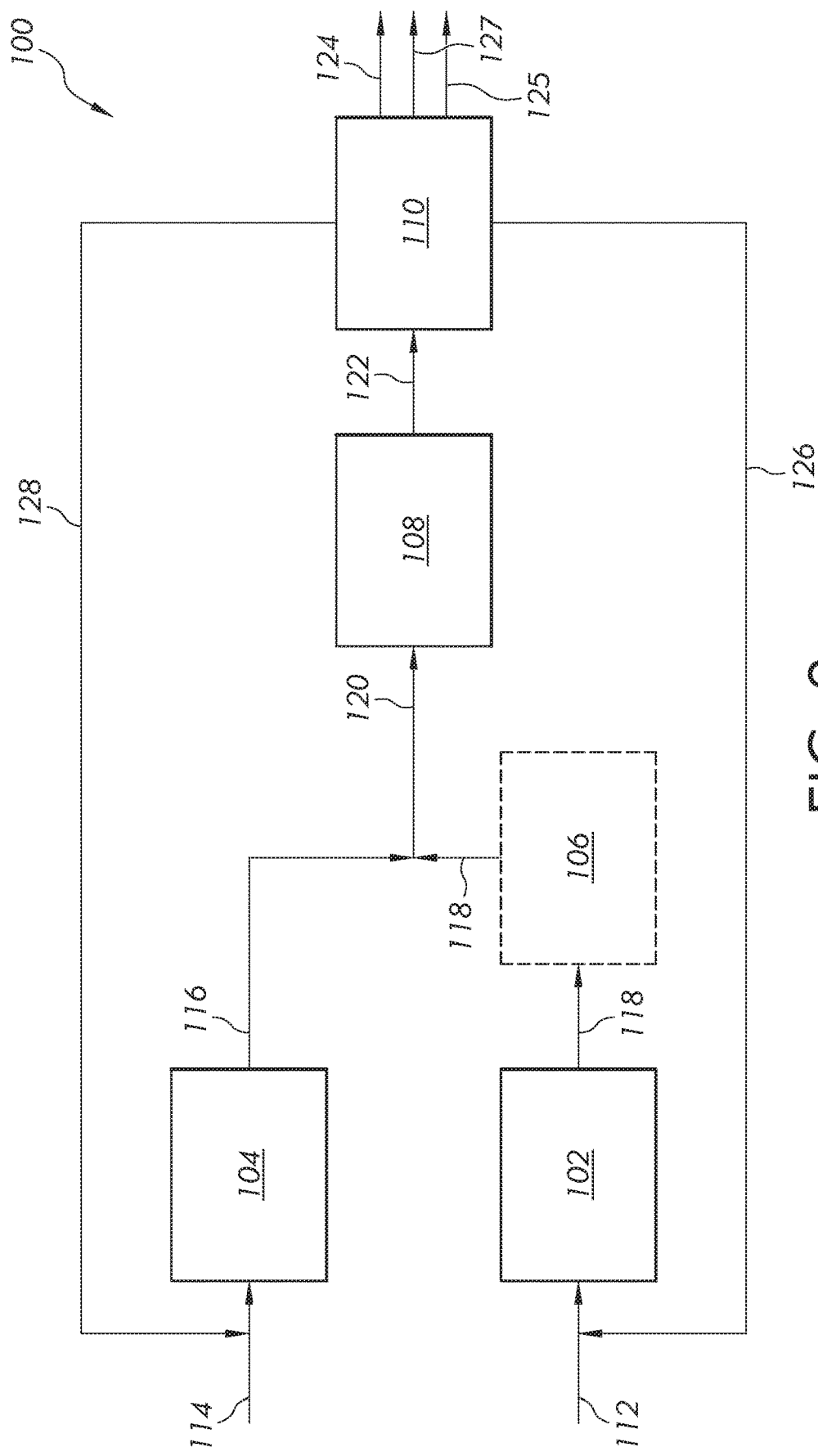
FIG. 2 schematically depicts a chemical conversion system flow chart, according to one or more embodiments described herein.

According to additional embodiments, the reactor system 102 may be integrated into a chemical conversion system 100, as depicted in FIG. 2. The chemical conversion system 100 may include a reactor system 102 as previously described, as well as a thermal cracking unit 104. System inlet stream 112 may bring feed materials to the reactor system 102, such as one or more of ethane, propane, butane, naphtha, or methanol. In some embodiments, system inlet stream 112 may be the feed stream of the described methods for forming olefins. System stream 118 may be produced by the reactor system 102, which may be the product stream of the presently described methods for forming olefins.

According to one or more embodiments, the chemical conversion system 100 may optionally include an oxygenates removal section 106 to process system stream 118. For example, an oxygenates removal section 106 may be utilized to remove one or more of methanol, water, or dimethyl ether from system stream 118 when a methanol-to-olefin reaction is utilized in reactor system 102. It should be understood that the oxygenates removal section 106 may be bypassed for when oxygenates are not present in the process stream 118, such as when dehydrogenation, cracking, or dehydration reactions are performed in the reactor system 102. The oxygenates removal section 106 may be any suitable separation unit, such as a tower or absorber.

Additionally, system inlet stream 114 may provide ethane, naphtha, propane, butane, or combinations thereof, to the thermal cracking unit 104. The thermal cracking unit 104 may include one or more furnaces. The system stream 116 formed by the thermal cracking unit 104 may be combined with system stream 118 to form system stream 120, which may enter a compression unit 108. The compression unit 108 may compress the contents of system stream 120 to form system stream 122. The compression unit 108 may include one or more of a series of compressors, a caustic tower, and a dryer. System stream 122 may be processed in a product recovery unit 110, which may recover light olefins such as ethene, butene, or propene from the chemical conversion system 100. Product recovery unit 110 may include one or more distillation towers or other separation devices. System outlet streams 124, 125, 127 may include one or more chemical products, such as ethene, propene, or butene, or other non-olefin materials which may be sold or further processed. In some embodiments, recycle streams 126 and 128 may recycle portions of system stream 122 back to the reactor system 102 and/or the thermal cracking unit 104, respectively. For example, recycle stream 126 may bring C4 hydrocarbons back to the reactor system 102.

Figure 3:
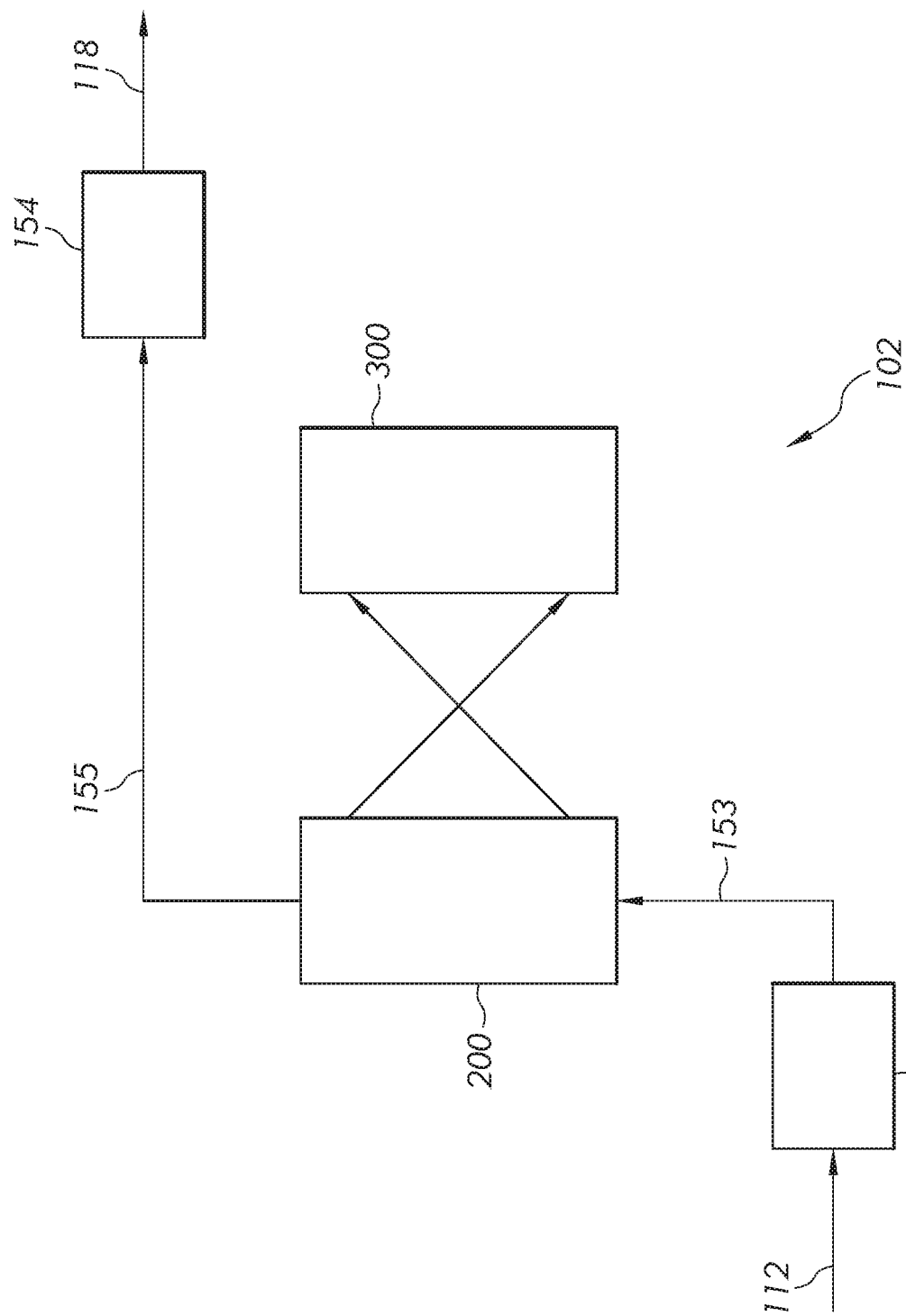
FIG. 3 schematically depicts a reactor system flow chart, according to one or more embodiments described herein.

According to one or more embodiments, now referring to FIGS. 2 and 3, the reactor system may further comprise one or more of a feed vaporizer 152 or a quench tower 154. The feed vaporizer may be upstream of the reactor portion 200 and the catalyst processing portion 300, and the quench tower 154 may be downstream of the reactor portion 200 and the catalyst processing portion 300. In such an embodiment, system stream 153 may provide feed materials to the reactor portion 200, and system stream 155 may pass product materials to the quench tower 154. In such an embodiment, the system stream 153 may constitute the feed stream and system stream 155 may constitute the product stream of the presently disclosed processes for forming olefins.

In one embodiment, the feed vaporizer 152 may vaporize the first feed stream and the second feed stream. In one or more embodiments, the feed vaporizer 152 may comprise one or more heat exchangers. As the first feed stream may be different from the second feed stream, the feed vaporizer 152 may be suitable for vaporizing both the first feed stream and the second feed stream. For example, the feed vaporizer 152 may be need to vaporize both relatively light feeds such as propane, medium feeds such as butane, or relatively heavy feeds such as naphtha. The feed vaporizer 152 may therefore be rated for vaporizing the heaviest feed contemplated, such as naphtha. For example, the feed vaporizer 152 may be a heat exchanger operable to utilize medium temperature quench water for vaporizing propane, operable to utilize hot quench water or low pressure steam to vaporize butane, and operable to utilize medium pressure steam to vaporize naphtha. As used herein, "medium pressure stream" refers to 100 psig to 800 psig steam, "low pressure steam" refers to 30 psig to 100 psig steam, "hot quench water" refers to water having a temperature of from 80° C. to 150° C., and "medium quench water" refers to water having a temperature of from 30° C. to 80° C.

According to additional embodiments, the quench tower 154 may be operable with water or oil as a quenching media. In one embodiment, the quench tower is a stripper like apparatus where the product stream is a vapor and the quenching media is the liquid. The quench tower 154 may serve to cool the product stream as well as strip it of contaminants. In some embodiments, such as when the product stream is relatively heavy like naphtha, an oil quench may be utilized to strip heavy hydrocarbons from the product stream. If such process were performed with a water quench, some water may condense and undesirably form two liquid phases of oil and water. For example, the quench tower may be designed to operate as a water quench for the ethane and/or propane dehydrogenation reactions, but may operate as an oil quench tower in the case of naphtha cracking, which may require some design modifications relative to a water quench tower. When the tower is operated as an oil quench tower, the booster compressor may need to be bypassed. The bottoms may be a heavy crude oil and could be sent to the combustor for supplemental fuel.

Now referring again to FIG. 2, in some embodiments, when ethylene is present in system inlet stream 114 and propane is present in the system inlet stream 112, ethane may be recycled via recycle stream 128 to the thermal cracking unit 108 and propane may be recycled via recycle stream 126 to the reactor system 102. In another embodiment, when ethane is present in system inlet stream 114 and system inlet stream 112, ethane may be recycled via recycle stream 128 to the thermal cracking unit 108 and/or ethane may be recycled via recycle stream 126 to the reactor system 102. In another embodiment, when ethane is present in system inlet stream 114 and butane is present in the system inlet stream 112, a produced C4 stream may be recycled via recycle stream 126 to the reactor system 102, and ethane may be recycled via recycle stream 128 to the thermal cracking unit 108. In another embodiment, when ethane is present in system inlet stream 114 and naphtha is present in the system inlet stream 112, a produced C4 stream may be recycled via recycle stream 126 to the reactor system 102, and ethane may be recycled via recycle stream 128 to the thermal cracking unit 108. In another embodiment, when ethane is present in system inlet stream 114 and methanol is present in the system inlet stream 112, ethane, propane, and butane may be recycled via recycle stream 128 to the thermal cracking unit 108, and a produced C4 stream may be sold.

The invention claimed is:

1. A method for processing chemical streams, the method comprising:
    operating a first chemical process comprising contacting a first feed stream with a first catalyst in a reactor wherein the reactor comprises an upstream reactor section and a downstream reactor section, the upstream reactor section having an average cross-sectional area that is at least 150% of the average cross-sectional area of the downstream reactor section, wherein the upstream reactor section operates as a fast fluidized, turbulent, or bubbling bed upflow reactor, and wherein the contacting of the first feed stream with the first catalyst causes a first reaction which forms a first product stream;
    stopping the first chemical process and removing the first catalyst from the reactor; and
    operating a second chemical process comprising contacting a second feed stream with a second catalyst in the reactor, wherein the contacting of the second feed stream with the second catalyst causes a second reaction which forms a second product stream;
wherein:
    the first reaction is a dehydrogenation reaction, a cracking reaction, a dehydration reaction, or a methanol-to-olefin reaction;
    the second reaction is a dehydrogenation reaction, a cracking reaction, a dehydration reaction, or a methanol-to-olefin reaction; and
    the first reaction and the second reaction are different types of reactions.

2. The method of claim 1, wherein the first product stream and the second product stream comprise one or more of ethylene, propylene, or butene.

3. The method of claim 1, wherein the first reaction or the second reaction is a dehydrogenation reaction, and the dehydrogenation reaction catalyst comprises gallium, platinum, or both.

4. The method of claim 1, wherein:
    the first reaction or the second reaction is a dehydrogenation reaction; and
    the dehydrogenation reaction feed stream comprises one or more of ethane, propane, n-butane, and i-butane.

5. The method of claim 1, wherein the first reaction or the second reaction is a cracking reaction, and the cracking reaction catalyst comprises one or more zeolites.

6. The method of claim 1, wherein:
    the first reaction or the second reaction is a cracking reaction; and
    the cracking reaction feed stream comprises one or more of naphtha, n-butane, or i-butane.

7. The method of claim 1, wherein the first reaction or the second reaction is a dehydration reaction, and the dehydration reaction catalyst comprises one or more acid catalysts.

8. The method of claim 1, wherein:
    the first reaction or the second reaction is a dehydration reaction;
    the dehydration reaction feed stream comprises one or more of ethanol, propanol, or butanol.

9. The method of claim 1, wherein the first reaction or the second reaction is a methanol-to-olefin reaction, and the methanol-to-olefin reaction catalyst comprises one or more zeolites.

10. The method of claim 1, wherein:
    the first reaction or the second reaction is a methanol-to-olefin reaction;
    the methanol-to-olefin feed stream comprises methanol.

11. The method of claim 1, wherein:
    operating the first chemical process further comprises passing the first product stream out of the reactor; and
    operating the second chemical process further comprises passing the second product stream out of the reactor.

12. The method of claim 1, wherein:
    operating the first chemical process further comprises recycling the first catalyst by passing the first catalyst from the reactor to a regeneration unit, processing the first catalyst in the regeneration unit, and passing the first catalyst from the regeneration unit to the reactor; and
    operating the second chemical process further comprises recycling the second catalyst by passing the second catalyst from the reactor to the regeneration unit, processing the second catalyst in the regeneration unit, and passing the second catalyst from the regeneration unit to the reactor.

13. The method of claim 1, wherein the first catalyst and the second catalyst have different compositions.

14. A method for processing chemical streams, the method comprising:
    operating a first chemical process comprising contacting a first feed stream with a first catalyst in a reactor, wherein the reactor comprises an upstream reactor section and a downstream reactor section, the upstream reactor section having an average cross-sectional area that is at least 150% of the average cross-sectional area of the downstream reactor section, and wherein the contacting of the first feed stream with the first catalyst causes a first reaction which forms a first product stream;
    stopping the first chemical process and removing the first catalyst from the reactor; and
    operating a second chemical process comprising contacting a second feed stream with a second catalyst in the reactor, wherein the contacting of the second feed stream with the second catalyst causes a second reaction which forms a second product stream;

wherein:
the first reaction is a dehydrogenation reaction and the second reaction is a cracking reaction.

15. The method of claim 14, wherein the upstream reactor section operates as a fast fluidized, turbulent, or bubbling bed upflow reactor.

16. A method for processing chemical streams, the method comprising:
operating a first chemical process comprising contacting a first feed stream with a first catalyst in a reactor, wherein the reactor comprises an upstream reactor section and a downstream reactor section, the upstream reactor section having an average cross-sectional area that is at least 150% of the average cross-sectional area of the downstream reactor section, and wherein the contacting of the first feed stream with the first catalyst causes a first reaction which forms a first product stream;
stopping the first chemical process and removing the first catalyst from the reactor; and
operating a second chemical process comprising contacting a second feed stream with a second catalyst in the reactor, wherein the contacting of the second feed stream with the second catalyst causes a second reaction which forms a second product stream;
wherein:
the first reaction is a cracking reaction and the second reaction is a dehydrogenation reaction.

17. The method of claim 16, wherein the upstream reactor section operates as a fast fluidized, turbulent, or bubbling bed upflow reactor.

* * * * *